(12) United States Patent
Jeffrey

(10) Patent No.: US 9,163,033 B2
(45) Date of Patent: Oct. 20, 2015

(54) NITROGEN-CONTAINING HETEROCYCLIC COMPOUNDS AND METHODS OF MAKING THE SAME

(71) Applicant: Christopher S. Jeffrey, Reno, NV (US)

(72) Inventor: Christopher S. Jeffrey, Reno, NV (US)

(73) Assignee: Board of Regents of the Nevada System of Higher Education, on Behalf of the University of Nevada, Reno, Reno, NV (US)

( * ) Notice: Subject to any disclaimer, the term of this patent is extended or adjusted under 35 U.S.C. 154(b) by 0 days.

(21) Appl. No.: 14/459,126

(22) Filed: Aug. 13, 2014

(65) Prior Publication Data

US 2014/0350246 A1 Nov. 27, 2014

Related U.S. Application Data

(63) Continuation of application No. 13/450,914, filed on Apr. 19, 2012, now abandoned.

(60) Provisional application No. 61/476,933, filed on Apr. 19, 2011.

(51) Int. Cl.
```
C07D 223/14    (2006.01)
C07D 265/12    (2006.01)
C07D 401/00    (2006.01)
C07D 498/08    (2006.01)
C07D 221/22    (2006.01)
```

(52) U.S. Cl.
CPC ............ *C07D 498/08* (2013.01); *C07D 221/22* (2013.01)

(58) Field of Classification Search
CPC ... C07D 265/12; C07D 223/14; C07D 401/00

USPC .................................. 544/93; 540/519, 524
See application file for complete search history.

(56) References Cited

U.S. PATENT DOCUMENTS

| | | | |
|---|---|---|---|
| 4,001,249 A | 1/1977 | Noyori et al. |
| 7,071,180 B2 | 7/2006 | Nilsson et al. |
| 7,534,794 B2 | 5/2009 | Nilsson et al. |
| 7,595,401 B2 | 9/2009 | Bajji et al. |
| 7,803,793 B2 | 9/2010 | Zhang et al. |
| 2004/0214232 A1 | 10/2004 | Burke et al. |
| 2009/0105296 A1 | 4/2009 | Illig et al. |
| 2010/0204463 A1 | 8/2010 | Liotta et al. |

OTHER PUBLICATIONS

Wu et al. (Organic Letters (2009), 11(12), 2707-2710).*
Gozalez-Alvarez et al. (European Journal of Organic Chemistry (1999), (11), 3085-3087).*
Gonzalez-Alvarez et al., "Diastereoselective Synthesis of a Precursor of Homocarbocyclic Nucleosides," *European Journal of Organic Chemistry*, (11)3085-3087, 1999.
Wu et al., "Brønsted Base-Modulated Regioselective Pd-Catalyzed Intramolecular Aerobic Oxidative Amination of Alkenes: Formation of Seven-Membered Amides and Evidence for Allylic C—H Activation," *Organic Letters*, 11(12), 2707-2710, 2009.

\* cited by examiner

*Primary Examiner* — Bruck Kifle
(74) *Attorney, Agent, or Firm* — Klarquist Sparkman, LLP

(57) ABSTRACT

The present invention relates to 7-membered nitrogen-containing heterocyclic compounds and methods of making the same. Using a novel aza-[4+3] cycloaddition reaction, the 7-membered heterocyclic compounds are synthesized by reacting a first reactant and a second reactant. Exemplary first reactants and second reactants include α-halohydroxamates and dienes, respectively.

4 Claims, No Drawings

NITROGEN-CONTAINING HETEROCYCLIC COMPOUNDS AND METHODS OF MAKING THE SAME

CROSS-REFERENCE TO RELATED APPLICATIONS

This application is a continuation application of the co-pending Non-Provisional patent application Ser. No. 13/450,914, which was filed on Apr. 19, 2012 and claimed the benefit of and priority to Provisional Application Ser. No. 61/476,933, filed Apr. 19, 2011, each of which is expressly incorporated herein by reference in its entirety.

FIELD OF THE INVENTION

The present invention relates generally to nitrogen-containing heterocyclic compounds and methods of making the same via a cycloaddition reaction.

BACKGROUND OF THE INVENTION

The [4+3] cycloaddition reaction of oxyallylcations with dienes has been intensively studied over the last five decades. This reaction has become a premier method for the construction of 7-membered carbocyclic compounds and has found numerous applications in target directed synthesis.

In addition to 7-membered carbocyclic compounds, 7-membered heterocyclic molecules, such as 7-membered nitrogen-containing heterocyclic compounds, are also of interest as targets possessing useful biological activity or as synthetic intermediates. However, a [4+3] cycloaddition reaction has yet to be developed to prepare 7-membered nitrogen-containing heterocyclic compounds.

Accordingly, a need exists for new 7-membered nitrogen-containing heterocyclic compounds and methods of synthesizing said 7-membered nitrogen-containing heterocyclic compounds.

SUMMARY OF THE INVENTION

This invention relates to nitrogen-containing heterocyclic compounds and methods of making the same. According to embodiments of the present invention, the nitrogen-containing heterocyclic compounds are 7-membered azacycles that are caprolactam derivatives, which are synthesized via a [4+3] cycloaddition reaction.

According to one embodiment of the present invention, a 7-membered nitrogen-containing heterocyclic compound is provided that is represented by the structural formula:

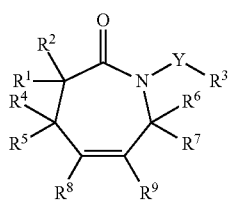

Formula (I)

wherein $R^1$ and $R^2$ are the same or different and are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, or $R^1$ and $R^2$ in combination form a cycloalkyl or a heterocycle; $R^3$ is a substituted or unsubstituted alkyl, acyl, aryl, alkaryl, alkenyl, alkynyl, cycloalkyl, heteroalkyl, heterocycle, sulfinyl, sulfonyl, or silyl; $R^4$, $R^5$, $R^6$, and $R^7$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxyl, acyloxy, thio, or silyl, wherein optionally $R^4$ and $R^6$, or $R^5$ and $R^7$ combine to form a bridging moiety in a cyclic substructure, the bridging moiety including at least one of carbon, oxygen, nitrogen, or sulfur, wherein optionally $R^4$ or $R^5$ are covalently bonded to $R^1$ or $R^2$, or wherein optionally $R^6$ or $R^7$ are covalently bonded to $R^3$; and $R^8$ and $R^9$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, or $R^8$ and $R^9$ combine to form a carbon-containing cyclic substructure; and Y is O, S, SO, or $NR^{10}$, wherein $R^{10}$ is a hydrogen, a substituted or unsubstituted alkyl, acyl, aryl, alkaryl, alkenyl, alkynyl, cycloalkyl, heteroalkyl, heterocycle, sulfinyl, sulfonyl, or silyl; wherein optionally $R^{10}$ is covalently bonded to $R^6$ or $R^7$.

According to another embodiment of the present invention, a [4+3] cycloaddition reaction product is provided, wherein the reaction product is derived from a first reactant represented by the general formula $R^1R^2XC\text{—}CO\text{—}NHYR^3$, wherein $R^1$ and $R^2$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, or $R^1$ and $R^2$ in combination form a cycloalkyl or a heterocycle; $R^3$ is a substituted or unsubstituted alkyl, acyl, aryl, alkaryl, alkenyl, alkynyl, cycloalkyl, heteroalkyl, heterocycle, sulfinyl, sulfonyl, or silyl; X is a leaving group; and Y is O, S, SO, or $NR^{10}$, wherein $R^{10}$ is a hydrogen, a substituted or unsubstituted alkyl, acyl, aryl, alkaryl, alkenyl, alkynyl, cycloalkyl, heteroalkyl, heterocycle, sulfinyl, sulfonyl, or silyl; and a second reactant, which is a diene.

According to yet another embodiment of the present invention, a method of making a nitrogen-containing heterocyclic compound via a [4+3] cycloaddition reaction is provided. The method includes combining a first reactant, a second reactant, and an activator to form a reaction mixture, and reacting the first reactant and the second reactant to form the N-containing cycloaddition reaction product. The first reactant has a chemical formula $R^1$, $R^2XC\text{—}CO\text{—}NHYR^3$, wherein $R^1$ and $R^2$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, or $R^1$ and $R^2$ in combination form a cycloalkyl or a heterocycle; $R^3$ is a substituted or unsubstituted alkyl, acyl, aryl, alkaryl, alkenyl, alkynyl, cycloalkyl, heteroalkyl, heterocycle, sulfinyl, sulfonyl, or silyl; X is a leaving group; and Y is O, S, SO, or $NR^{10}$, wherein $R^{10}$ is a hydrogen, a substituted or unsubstituted alkyl, acyl, aryl, alkaryl, alkenyl, alkynyl, cycloalkyl, heteroalkyl, heterocycle, sulfinyl, sulfonyl, or silyl. The second reactant includes a diene moiety.

DETAILED DESCRIPTION OF EMBODIMENTS OF THE INVENTION

Embodiments of the present invention are directed to novel 7-membered azacyclic compounds and methods of making the same. The compounds may possess useful biological activity or be useful as intermediates in the targeted synthesis of biologically active compounds.

A 7-membered nitrogen-containing heterocyclic compound according to one embodiment of the present invention is represented by the structural formula (I):

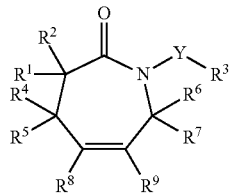

Formula (I)

wherein $R^1$ and $R^2$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, or $R^1$ and $R^2$ in combination form a cycloalkyl or a heterocycle; $R^3$ is a substituted or unsubstituted alkyl, acyl, aryl, alkaryl, alkenyl, alkynyl, cycloalkyl, heteroalkyl, heterocycle, sulfinyl, sulfonyl, or silyl; $R^4$, $R^5$, $R^6$, and $R^7$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, wherein optionally $R^4$ or $R^5$ and $R^6$ or $R^7$ combine to form a bridging moiety to form a cyclic substructure, wherein the bridging moiety includes at least one of carbon, oxygen, nitrogen, or sulfur, wherein optionally $R^4$ or $R^5$ are covalently bonded to $R^1$ or $R^2$, or wherein optionally $R^6$ or $R^7$ are covalently bonded to $R^3$; $R^8$ and $R^9$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, or $R^8$ and $R^9$ combine to form a carbon-containing cyclic substructure; and Y is O, S, SO, or $NR^{10}$, wherein $R^{10}$ is a hydrogen, a substituted or unsubstituted alkyl, acyl, aryl, alkaryl, alkenyl, alkynyl, cycloalkyl, heteroalkyl, heterocycle, sulfinyl, sulfonyl, or silyl; and wherein optionally $R^{10}$ is covalently bonded to $R^6$ or $R^7$.

In one embodiment, the 7-membered nitrogen-containing heterocyclic compound can be represented by structural formula (II),

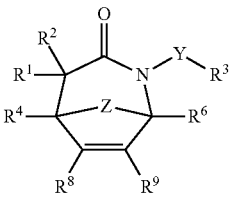

Formula (II)

wherein $R^1$ and $R^2$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl; $R^3$ is a substituted or unsubstituted alkyl, acyl, aryl, alkaryl, alkenyl, alkynyl, cycloalkyl, heteroalkyl, heterocycle, sulfinyl, sulfonyl, or silyl; $R^4$ and $R^6$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, wherein optionally $R^4$ is covalently bonded to $R^1$ or $R^2$, or wherein optionally $R^6$ is covalently bonded to $R^3$; $R^8$ and $R^9$ are independently selected from hydrogen, halide, a substituted or un-substituted alkyl, aryl, acyl, alkaryl, alkenyl, alkynyl, cycloalkyl, heteroalkyl, heterocycle, amino, amido, acyloxy, thio, or silyl, or $R^8$ and $R^9$ combine to form a carbon-containing cyclic substructure; Y is O, S, SO, or $NR^{10}$, wherein $R^{10}$ is a hydrogen, a substituted or unsubstituted alkyl, acyl, aryl, alkaryl, alkenyl, alkynyl, cycloalkyl, heteroalkyl, heterocycle, sulfinyl, sulfonyl, or silyl; and Z comprises at least one of carbon, oxygen, nitrogen, or sulfur.

In another example, the 7-membered nitrogen-containing heterocyclic compound of formula (I), which may also be referred to as a caprolactam derivative, may be alternatively represented by structural formulas (III) through (VIII).

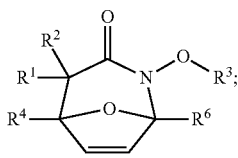

(III)

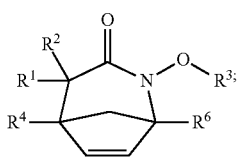

(IV)

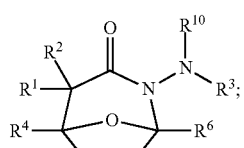

(V)

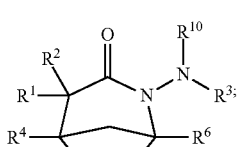

(VI)

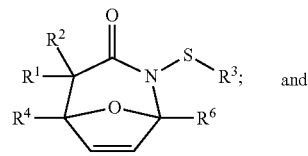

(VII)

and

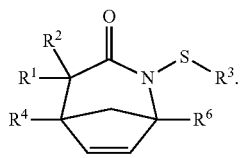

(VIII)

According to one embodiment of the present invention, the compounds of structural formulas (I) through (VIII) can be synthesized by exploiting reactions of a first reactant-derived electrophilic nitrogen species, including an aza-oxyallylcationic intermediate. As shown in Scheme 1, a reactive intermediate aza-oxyallylcation (1) can undergo a cyclization reaction with an appropriate second reactant (2) to synthesize a 7-membered nitrogen-containing heterocyclic compound (3), which is a heterocyclic motif that is widely represented in natural products, pharmaceuticals, peptidomimetics, and monomers for polymerization. The reaction of an aza-oxyallylcation (1) with the second reactant (2), which includes a diene moiety, to form a 7-membered nitrogen-containing heterocyclic compound (3) can be referred to as an aza-[4+3] cycloaddition reaction.

(Scheme 1)

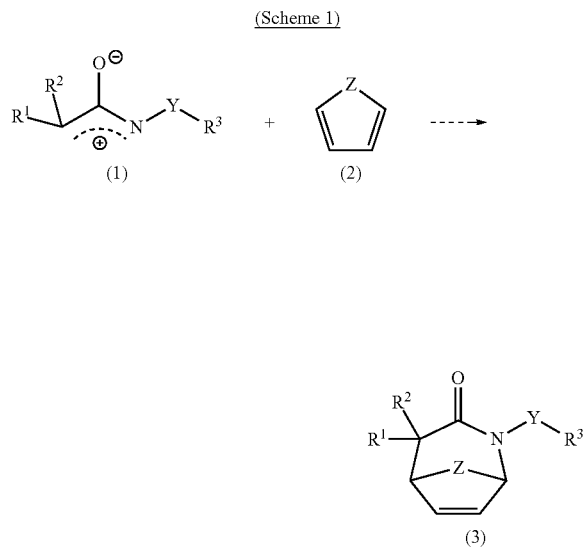

When the second reactant (2) is itself a cyclic diene compound, such as cyclopentadienes, 1,3-cyclohexadienes, pyrroles, or furans, the resultant heterocyclic compound is a bicyclic compound, such as that shown in the 7-membered nitrogen-containing heterocyclic compound (3). The variables are as defined above. In particular, see the first reactant for (1); and formula (II) for both (3) and Z in (2).

In accordance with one embodiment of the invention, the requisite aza-oxyallylcation (1) can be obtained by a dehydrohalogenation of an α-halohydroxamate or its equivalent. Accordingly, α-halohydroxamates amenable to forming a 7-membered nitrogen-containing heterocyclic compound include those represented by the general formula $R^1R^2XC-CO-NHYR^3$. Accordingly, $R^1$ and $R^2$ are bonded to a carbon atom adjacent a carbonyl, i.e., the α-carbon, and are independently selected from hydrogen, halide, a substituted or unsubstituted alkyl, acyl, aryl, alkaryl, alkenyl, alkynyl, cycloalkyl, heteroalkyl, heterocycle, amino, amido, alkoxy, acyloxy, thio, or silyl, or $R^1$ and $R^2$ in combination form a cycloalkyl or a heterocycle. Further, $R^3$ can be a substituted or unsubstituted alkyl, acyl, aryl, alkaryl, alkenyl, alkynyl, cycloalkyl, heteroalkyl, heterocycle, sulfinyl, sulfonyl, or silyl; X is a leaving group such as a sulfonate (e.g., mesylate or tosylate) or halide; and Y is O, S, SO, or $NR^{10}$, wherein $R^{10}$ is hydrogen, a substituted or unsubstituted alkyl, acyl, aryl, alkaryl, alkenyl, alkynyl, cycloalkyl, heteroalkyl, heterocycle, sulfinyl, sulfonyl, or silyl.

It should be further appreciated that $R^3$ and/or $R^{10}$ may include a chiral moiety or chiral auxiliary that may induce chirality in the azacyclic cycloaddition reaction product.

Any suitable method of preparing the α-halohydroxamate or its equivalent can be used. For example, α-halo acid halides of a general formula $R^1R^2XC-CO-X$ may be reacted with the appropriate nucleophilic reactant, wherein $R^1$ and $R^2$ are independently selected from hydrogen, halide, a substituted or un-substituted alkyl, aryl, alkaryl, alkenyl, alkynyl, cycloalkyl, heteroalkyl, or heterocycle, or $R^1$ and $R^2$ in combination form a cycloalkyl or a heterocycle; X is a halide. For example, 2-bromo-2-methylpropanoyl bromide or 2-bromobutyryl bromide are suitable α-halo acid halides. Exemplary nucleophilic reactants include those of a general formula $NH_2YR^3$, wherein $R^3$ is a substituted or unsubstituted alkyl, acyl, aryl, alkaryl, alkenyl, alkynyl, cycloalkyl, heteroalkyl, heterocycle, sulfinyl, sulfonyl, or silyl; Y is O, S, SO, or $NR^{10}$, wherein $R^{10}$ is hydrogen, a substituted or unsubstituted alkyl, acyl, aryl, alkaryl, alkenyl, alkynyl, cycloalkyl, heteroalkyl, heterocycle, sulfinyl, sulfonyl, or silyl. For example, O-benzylhydroxylamine or O-methylhydroxylamine are suitable nucleophilic reactants.

As stated above, $R^3$ may comprise a chiral moiety or chiral auxiliary that may induce chirality in the azacyclic cycloaddition reaction product. In the absence of asymmetric induction, the azacyclic cycloaddition product is produced as a racemic mixture. As such, according to one embodiment, the nucleophilic reactant of the general formula $NH_2YR^3$ may include a chiral 3-amino-2-oxazolidone, chiral hydroxylamine derivatives such as (R)-(2,2-dimethyl-[1,3]dioxolan-4-ylmethyl)-hydroxylamine, chiral hydrazines such as 5-hydrazino-2,4-dinitrophenyl-L-alaninamide, or chiral sulfonamides such as (R)-(+)-2-methyl-2-propanesulfinamide, for example. In another embodiment, $R^{10}$ may comprise a chiral moiety or chiral auxiliary.

Activators are used to effect the dehydrohalogenation of the α-halohydroxamates. Exemplary activators include, but are not limited to bases, such as amine bases and carbonates. Exemplary amine bases, include tertiary amines such as triethylamine or 1,4-diazabicyclo[2.2.2]octane (DABCO). Exemplary carbonate bases include alkali metal carbonate salts such as sodium, potassium or cesium carbonate. Other useful additives that can be useful in the dehydrohalogenation process include lewis acids, such a lithium perchlorate. The amount of activator relative to the α-halohydroxamate may vary. For example, bases such as triethylamine or sodium carbonate may be used from about one stoichiometric equivalent or more. In one example, two (2) stoichiometric equivalents of base were included in the aza-cycloaddition reaction mixture.

Suitable solvents include conventional solvents wherein the α-halohydroxamates are at least partially soluble. Exemplary solvents include polar protic, polar aprotic, and non-polar solvents. For polar protic solvents, it may be advantageous to use halogenated polar protic solvents to reduce the nucleophilicity of the solvent, which can suppress undesirable side reactions between the solvent and the α-halohydroxamates. Exemplary halogenated polar protic solvents include trifluoroethanol (TFE) and hexafluoroisopropanol (HFIP). Other suitable solvents include diethyl ether, tetrahydrofuran (THF), dichloromethane (DCM), acetonitrile (ACN), nitromethane ($MeNO_2$), or N-methylpyrrolidinone (NMP), for example. The amount of solvent, relative to the first and second reactants, may be varied to provide a desired concentration of reactants.

According to embodiments of the invention, the second reactant includes a diene compound represented by a general formula $R^4R^5C=CR^8-CR^9=CR^6R^7$, wherein $R^4$, $R^5$, $R^6$, and $R^7$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, or wherein optionally ($R^4$ or $R^5$) and ($R^6$ or $R^7$) combine to form a bridging moiety to form a cyclic substructure, wherein the bridging moiety includes at least one of carbon, oxygen, nitrogen, or sulfur; $R^8$ and $R^9$ are independently selected from hydrogen, halide, a substituted or un-substituted alkyl, acyl, aryl, alkaryl, alkenyl, alkynyl, cycloalkyl, heteroalkyl, heterocycle, amino, amido, alkoxy, acyloxy, thio, or silyl, or $R^8$ and $R^9$ combine to form a carbon-containing cyclic substructure. Additionally or alternatively, $R^4$ or $R^5$ can be covalently bonded to the α-carbon of the first reactant through $R^1$ or $R^2$, or that $R^6$ or $R^7$ can be covalently bonded to $R^3$ (or $R^{10}$ where Y is $NR^{10}$) of the first reactant, either of which would yield a complementary bicyclic or tricyclic cycloaddition product to that from using acyclic or cyclic dienes, respectively. Exemplary dienes include, but are not limited to, furan, cyclopentadiene, N-substituted pyrroles (e.g., N-acyl, N-sulfonyl, N-alkyl, or N-silyl), or 1,3-cyclopentadiene.

The second reactant, which includes the diene moiety, may also be used as a co-solvent, if desired. For example, simple and inexpensive diene compounds, such as cyclopentadiene or furan, may be use as a co-solvent thereby providing a large excess of the diene. In one example, furan or cyclopentadiene may be used in 1:1 v/v with the aforementioned solvents.

The method of making a 7-membered azacyclic compound via an aza-[4+3] cycloaddition reaction includes combining the first reactant, the second reactant, and the activator to form a reaction mixture, and reacting the first reactant and the second reactant to form the 7-membered azacyclic reaction product. According to one embodiment of the present invention, the first reactant is a compound represented by the general formula $R^1R^2XC$—CO—$NHYR^3$; the second reactant includes a diene represented by the general formula $R^4R^5C$=$CR^8$—$CR^9$=$CR^6R^7$; and the activator may include an amine base or a carbonate salt. The variables are as defined above. The reacting of the first reactant and the diene reactant is initiated by the action of activator to effect the dehydrohalogenation of the first reactant.

The reaction temperatures may range from above the freezing point of the reaction mixture to about the reflux temperature of the reaction mixture at ambient pressure. If higher temperatures are needed, then the reaction vessel may be pressurized. Accordingly, the reaction temperature may begin at a first temperature and subsequently changed to a second temperature or a temperature range. For example, the reactants and activator may be combined at about 0° C. and then passively and/or actively warmed to about 25° C.

The reaction may be performed over a wide temperature range from about 0° C. to about 60° C. In one example, the reaction mixture may be maintained at a temperature of about 15° C. to about 45° C. In another example, the reaction is performed at room temperature. In yet another example, the reaction mixture is first cooled to about 0° C. and then subsequently warmed to room temperature or above.

While not specifically required, the reaction may be performed under an inert atmosphere. For example, inert gases, such as nitrogen or argon, may be used to purge the reaction vessel prior to charging reagents. Alternatively, the reaction vessel can be maintained under a positive pressure of inert gas over the course of the reaction.

Reaction times may vary depending on a variety of factors, such as reaction temperature, reaction concentration, solvent, nature of the activator, presence of additives, electronic and/or steric effects of the reactants, and the like. Accordingly, the reaction time may be from about 15 minutes to about 72 hours, or until at least one of the reactants is substantially consumed. For example, the reaction time may be from about 0.5 to about 16 hours at room temperature.

The present invention is illustrated by the following examples that are merely for the purpose of illustration and are not to be regarded as limiting the scope of the invention or the manner in which it can be practiced.

General Experimental:

All reactions were carried out under an atmosphere of nitrogen in oven-dried glassware with magnetic stirring, unless otherwise specified. Dichloromethane was purified by passage through a bed of activated alumina. Cyclopentadiene was distilled from dicyclopentadiene immediately prior to use. All other reagents and solvents were purchased from Sigma-Aldrich Chemical Company and used without any further purification. Thin-layer chromatography (TLC) information was recorded on Silicycle glass 60 F254 plates and developed by staining with $KMnO_4$ or ceric ammonium molybdate. Purification of reaction products was carried out by flash chromatography using Silicycle Siliaflash® P60 (230-400 mesh). $^1$H-NMR spectra were measured on Varian 400 (400 MHz), Varian MR400 (400 MHz), or Varian 500 (500 MHz) spectrometers and are reported in ppm (s=singlet, d=doublet, t=triplet, q=quartet, m=multiplet, br=broad; integration; coupling constant(s) in Hz), using Tetramethylsilane (TMS) as an internal standard (TMS at 0.00 ppm) in CDCl3 or the solvent peak (1.94 ppm) in $CD_3CN$. $^{13}$C-NMR spectra were recorded on V400 or V500 spectrometer and reported in ppm using solvent as an internal standard (CDCl3 at 77.16 ppm) or ($CD_3CN$ at 118.26 ppm). Infrared (IR) spectra were recorded on a Nicolet 6700 FT-IR with a diamond ATR and data are reported as cm-1 (br=broad, s=strong). High-resolution mass spectra (HRMS) were obtained using an Agilent 6230 TOF LC/MS with an (atmospheric pressure photoionization (APPI) or electrospray (ESI) source with purine and HP-0921 as an internal calibrants. HRMS data of α-halohydroxamates were obtained with an inlet temperature of 200° C.

The substrate scope of the aza-[4+3] cycloaddition reaction was explored using various α-halohydroxamates 4a-k with exemplary diene reactants, e.g., furan or cyclopentadiene. All reactions were conducted in solvent:furan or cyclopentadiene (1:1 v/v, 0.25 M) at 0° C. to 25° C. with triethylamine (TEA) (2.0 equivalents). Trifluoroethanol (TFE) and hexafluoroisopropanol (HFIP) were studied as exemplary solvents. Diastereoisomeric ratio (d.r.) was determined from crude $^1$H NMR analysis. ≥19:1 d.r. indicates that the minor diastereoisomer was not detected by this analysis. The chemical yield shown in Table 1 is that of the isolated cycloadduct 5.

TABLE 1
Exemplary aza-[4 + 3] cycloaddition reactions of α-halohydroxamates with cyclopentadiene or furan.
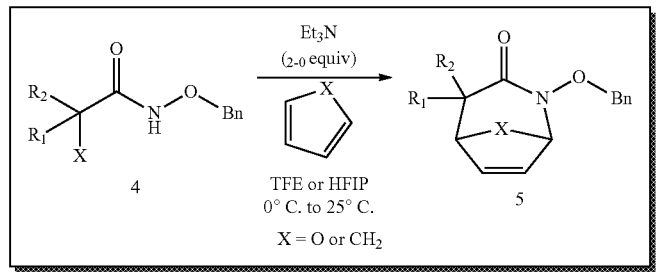
| entry | solvent reaction time | substrate | product d.r. (endo:exo) | yield[a] |
|---|---|---|---|---|
| a<br>b<br>c | TFE<br>16 h | | | R = Me (67%)<br>R = Et (86%)<br>R = t-Bu (54%) |
| d | TFE<br>48 h | | | 78% |
| e | TFE<br>72 h | | | 73% |
| f | TFE<br>1 h | | | 52% |
| g | HFIP<br>30 min | | | 78% |
| h | HFIP<br>30 min | | | 65% |

TABLE 1-continued

Exemplary aza-[4 + 3] cycloaddition reactions of α-halohydroxamates with cyclopentadiene or furan.

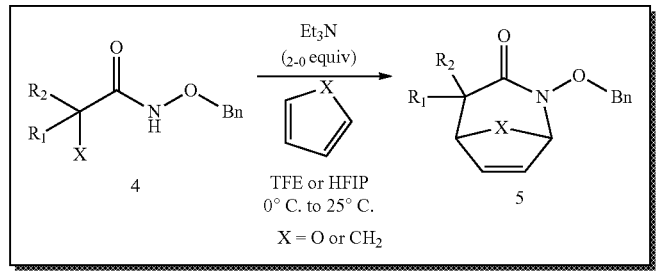

| entry | solvent reaction time | substrate | product d.r. (endo:exo) | yield[a] |
|---|---|---|---|---|
| i | TFE 16 h | | | 85% |
| j | TFE 16 h | | | 64% |
| k | HFIP 30 min | | | 81% |

The general procedure (A) for the synthesis of the α-halohydroxamates 4a-h is as follows:

To a suspension of the O-benzyloxyamine hydrochloride and triethylamine (TEA) in $CH_2Cl_2$ (0.25 M) was added dropwise the α-haloacid halide at 0° C. The reaction mixture was stirred at this temperature until TLC analysis (3:1) hexanes:ethyl acetate (EtOAc) revealed complete consumption of starting material. The mixture was warmed to room temperature and quenched with water. The organic phase was washed 3 times with water, dried over sodium sulfate, filtered and evaporated. Purification via recrystallization from hexanes:EtOAc or via a column chromatography ($SiO_2$, 3:1, hexanes:EtOAc) provided the α-halohydroxamates in 45-90% yield as a colorless solids.

The general procedure (B) for the aza-[4+3] cycloaddition reaction of furan or cyclopentadiene in trifluoroethanol (TFE) or hexafluoroisopropanol (HFIP) is as follows:

To a solution of α-halohydroxamate (1 equiv) in TFE and furan [1:1 (v/v) 0.25 M] or $(CF_3)_2CHOH$ was added TEA (2 equivalents) drop-wise at 0° C. The solution was allowed to warm to room temperature and the reaction progress was monitored by TLC (3:1 or 2:1 hexanes:EtOAc) until complete consumption of the α-halohydroxamate. The volatiles were removed under reduced pressure and the residue was purified via flash column chromatography (4:1 to 3:1, hexanes:EtOAc) to provide the cycloadducts as oils (54-85% yield).

2-bromo-2-methyl-N-(phenylmethyl)propanamide: Prepared in 91% yield (10.7 g, 42 mmol) from the reaction of 2-bromo-2-methylpropanoyl bromide (10.6 g, 46 mmol) with benzylamine (5.1 mL, 46 mmol) via general procedure A. Rf=0.84 (3:1, hexanes:EtOAc); mp 73.4-75.5° C.; 1H NMR (400 MHz, CDCl3): δ 7.41-7.23 (m, 1H), 7.03 (br s, 1H), 4.46 (d, J=5.8 Hz, 1H), and 1.99 (s, 1H); 13C NMR (125 MHz, CDCl3): δ 172.0, 137.8, 128.8, 127.6, 127.6, 62.8, 44.4, and 32.6; IR (neat) 3291 (br), 3065, 301, 3008, 2938, 2919, 1642 (s), 1533 cm-1; HRMS (ESI) calculated 256.0332 C11H15BrNO [M+H]+, observed 256.0329.

(±)-2-bromo-N-(phenylmethoxy)propanamide (4a): Prepared in 53% yield (631 mg, 2.44 mmol) from the reaction of 2-bromo-2-methylpropanoyl bromide (1.0 g, 4.6 mmol) with O-benzylhydroxylamine hydrochloride (742 mg, 4.6 mmol) via general procedure A. Rf=0.28 (3:1, hexanes:EtOAc); mp=75.3-77.4° C.; 1H-NMR (500 MHz, CDCl3): δ 9.61 (br s, 1H), 7.44-7.26 (m, 5H), 4.90 (s, 2H), 4.31 (q, J=7.7 Hz, 1H), and 1.77 (d, J=6.4 Hz, 3H); 13C-NMR (126 MHz, CDCl3): δ 167.5, 134.8, 129.45, 128.9, 128.7, 78.3, 40.5, and 22.2; FT-IR (neat) 3110 (br), 2924, 2852, 1675 (s), 1508, 1495, 1453, 1364, 1188, 1038, 1023 cm-1;

(±)-2-bromo-N-(phenylmethoxy)butanamide (4b, 4i): Prepared in 72% yield (4.71 g, 17.3 mmol) from the reaction of 2-bromobutyryl bromide (5.0 g, 24 mmol) with O-benzylhydroxylamine, hydrochloride via general procedure A. Rf=0.49 (3:1, hexanes:EtOAc); mp=99.3-101.6° C.; 1H-NMR (500 MHz, CDCl3): δ 8.92 (br s, 1H), 7.52-7.31 (m, 5H), 4.93 (s, 2H), 4.12 (app q, J=7.2 Hz 1H), 2.02-1.94 (m, 2H), and 1.00 (t, J=7.0 Hz, 3H); 13C-NMR (126 MHz, CDCl3): δ 166.6, 134.8, 129.5, 129.0, 128.7, 78.4, 48.8, 28.8, and 11.8; FT-IR (neat) 3112, 2963, 2933, 2874, 1695, 1668 (s), 1528, 1496, 1454, 1364, 1177, 1089, 1023 cm-1. HRMS calculated for C11H15BrNO [M+H]+, 256.0332; found 256.0329.

(±)-2-bromo-2,2-dimethyl N-(phenylmethoxy)butanamide (4c): Prepared in 61% yield (3.5 g, 11.8 mmol) from the reaction of 2-bromo-2,2-dimethylpropanoyl chloride (4.98 g, 19.3 mmol) with O-benzylhydroxylamine (3.12 g, 19.3 mmol), hydrochloride via general procedure A. Rf=0.33 (3:1, hexanes:EtOAc); 1H-NMR (500 MHz, CDCl3): δ 8.73 (br s, 1H), 7.55-7.29 (m, 4H), 4.92 (s, 2H), 3.95 (s, 1H), 1.11 (s, 9H); 13C-NMR (126 MHz, CDCl3): δ 166.1, 135.0, 129.6, 129.0, 128.8, 78.3, 59.4, 35.2, and 27.4; FT-IR (neat): 3179 (br), 3037, 2985, 2960, 2944, 2885, 1657 (s), 1511, 1479, 1371, 1241, 1159, 1052 cm-1; HRMS ESI-MS calculated for C13H19BrNO2 (M+H)+ 300.0594, observed 300.0595.

(±)-2-chloro-N-(phenylmethoxy)propanamide (4d): Prepared in 48% yield (0.97 g, 3.9 mmol) from the reaction of 2-chloropropanoyl chloride (1.03 g, 8.2 mmol) with O-benzylhydroxylamine, hydrochloride (1.03 g, 8.2 mmol) via general procedure A. Rf=0.43 (3:1, hexanes:EtOAc); mp=70.1-72.8° C.; 1H-NMR (500 MHz, CDCl3): δ 9.09 (br s, 1H), 7.44-7.35 (m, 5H), 4.93 (s, 4H), 4.33 (q, J=7.1 Hz, 1H), and 1.69 (d, J=6.8 Hz, 3H); 13C-NMR (126 MHz, CDCl3): δ 167.1, 134.8, 129.5, 129.1, 128.8, 78.5, 53.2, and 22.3; FT-IR: (neat): 3112 (br), 2931, 1678 (s), 1494, 1454, 1364, 1222, 1204, 1074 cm-1. HRMS ESI-MS: calculated for C10H12ClNNaO2 (M+Na)+, 236.0449; found 236.0445.

2,2-dichloro-N-(phenylmethoxy)acetamide (4e, 4j): Prepared in 82% yield (2.6 g, 11.1 mmol) from the reaction of 2,2-dichloroacetyl chloride (2.0 g, 13.6 mmol) with O-benzylhydroxylamine, hydrochloride (2.15 g, 13.6 mmol) via general procedure A. Rf=0.52 (3:1, hexanes:EtOAc); 1H NMR (400 MHz, CD3CN) δ 9.89 (br s, 1H), 7.63-7.17 (m, 4H), 6.02 (s, 1H), and 4.89 (s, 2H); 13C NMR (101 MHz, CD3CN) δ 162.2, 136.1, 130.4, 129.7, 129.4, 78.8, and 65.6; IR (film) 3135 (br), 2996, 2880, 2860, 1700, 1677 (st), 1531, 1468, 1454, 1367, 1341, 1214, 1200, 1046, 1027 cm-1; HR-APPIMS calculated for C9H9Cl2NO2 (M*)+233.0005, observed 232.9976.

(±)-2-chloro-2-(4-chlorophenyl)acetamide (4f): A suspension of the epoxynitrile (315 mg, 1.2 mmol, ~80% pure) and Obenzylhydroxylamine hydrochloride (240 mg, 1.5 mmol) in acetonitrile (15 mL, 0.1 M) was heated to reflux overnight. The suspension was cooled and the mixture was concentrated to 5 mL. The residue was partitioned between water and ethylacetate and the aqueous phase was extracted (3×15 mL). The combined organic phase was washed with brine (15 mL), dried over Na2SO4, filtered, and evaporated under reduced pressure. The residue was recrystallized from hexanes and EtOAc to provide the product as a colorless solid (215 mg, 0.69 mmol, 58% yield). Rf=0.20 (3:1, hexanes:EtOAc); 1H NMR (400 MHz, CD3CN) δ 9.76 (s, 1H), 7.51-7.29 (m, 9H), 5.27 (s, 1H), and 4.84 (s, 2H). 13C NMR (101 MHz, CD3CN) δ 165.2, 136.6, 136.3, 135.5, 130.6, 130.4, 129.8, 129.6, 129.4, 78.6, and 57.9; IR (neat): 3115.8 (br), 2942, 2842, 2662, 1492 (s); HR-ESIMS calculated for C15H13Cl2NNaO2 (M+Na)+332.0216, observed 332.0216.

2-bromo-2-methyl-N-(phenylmethoxy)propanamide (4g): Prepared in 87% yield (3.53 g, 11.3 mmol) from the reaction of 2-bromo-2-methylpropanoyl bromide (3.0 g, 13 mmol) with O-benzylhydroxylamine hydrochloride (2.13 g, 13 mmol) via general procedure A. Rf=0.58 (3:1, hexanes:EtOAc); mp=88.6-91.1° C.; 1H-NMR (500 MHz, CDCl3): δ 9.05 (br s, 1H), 7.45-7.34 (m, 5H), 4.94 (s, 2H), and 1.93 (s, 6H); 13C-NMR (126 MHz, CDCl3): δ 169.7, 134.9, 129.6, 129.1, 128.8, 78.4, 59.5, and 32.6; FT-IR (neat) 3195 (br), 3034, 2954, 2890, 1652 (s), 1505, 1469, 1454, 1112, 1032, 1004 cm-1. HRESI-MS: calcd ☐ for C11H18BrN2O2 (M+NH4)+ 289.0546, observed 289.0543.

(±)-2-bromo-N-(phenylmethoxy)carboxamide (4h, 4k): Prepared in 72% yield (4.5 g, 14.5 mmol) from the reaction of 2-bromocyclohexanoyl bromide (4.53 g, 20.1 mmol) with O-benzylhydroxylamine, hydrochloride (3.21 g, 20.1 mmol) via general procedure A. Rf=0.47 (3:1; hexanes:EtOAc); mp=84.6-86.1° C.; 1H NMR (400 MHz, CDCl3) δ 8.98 (br s, 1H), 7.51-7.31 (m, 5H), 4.94 (s, 2H), 2.13 (ddd, J=14.6, 10.9, 4.0 Hz, 2H), 2.00 (dt, J=14.0, 4.1 Hz, 2H), 1.80-1.57 (m, 5H), 1.42-1.23 (m, 1H). 13C NMR (101 MHz, CDCl3) δ 169.6, 135.0, 129.6, 129.0, 128.7, 78.2, 38.1, 24.7, 22.6. IR (neat) 3235 (br), 3034, 2936, 2862, 1680, 1651 (s), 1470, 1459, 1270, 1249, 1210, 1122, 1025, 1000 cm-1; HR-APPIMS calculated for C14H16BrNO2 (M+H)+ 312.0594, observed 312.0206.

(±)-(4S,5R,1S) 4-methyl-8-oxo-2-(phenylmethoxy)-2-azabicyclo[3.2.1]oct-6-en-3-one (5a): Prepared in 67% yield (63.3 mg, 0.26 mmol) from the reaction of 2-bromo-N-(phenylmethoxy)propanamide (100.7 mg, 0.39 mmol) with furan via general procedure B. Rf=0.3 (3:1, hexanes:EtOAc); 1H-NMR (500 MHz, CDCl3): δ 7.47-7.32 (m, 5H), 6.57 (dd, J=6.2, 1.0 Hz, 1H), 6.41 (dd, J=6.0, 1.7 Hz, 1H), 5.25 (d, J=1.5 Hz, 1H), 5.00 (d, J=11.0 Hz, 1H), 4.87 (d, J=11.0 Hz, 1H), 4.85 (dd, J=5.0, 1.9 Hz, 1H), 3.17 (qd, J=7.4, 5.0 Hz, 1H), and 1.09 (d, J=7.4 Hz, 3H); 13C-NMR (126 MHz, CDCl3): δ 172.7, 136.1, 135.8, 133.8, 129.7, 128.9, 128.7, 91.6, 82.9, 78.1, 45.1, and 10.6; IR (film) 3089, 2970, 2970, 2934, 2876, 1697, 1497, 1455, 1377, 1209, 1053 cm-1; HRMS calculated for C14H16NO3 (M+H)+ 246.1125, observed 246.1118.

(±)-(4S,5R,1S) 4-ethyl-8-oxo-2-(phenylmethoxy)-2-azabicyclo[3.2.1]oct-6-en-3-one (5b): Prepared in 86% yield (40.6 mg, 0.157 mmol) from the reaction of 2-bromo-N-(phenylmethoxy)butanamide (50.0 mg, 0.183 mmol) with furan via general procedure B. Rf=0.3 (3:1, hexanes:EtOAc); Rf 0.50 (3:1, hexanes:ethyl acetate); 1H-NMR (500 MHz, CDCl3): δ 7.45-7.42 (m, 2H), 7.41-7.32 (m, 3H), 6.51 (dd, J=6.0, 1 Hz, 1H), 6.38 (dd, J=6.0, 1.8 Hz, 1H), 5.25 (d, J=1.2 Hz, 1H), 4.99 (d, J=11.0 Hz, 1H), 4.95 (dd, J=5.1, 1.8 Hz, 1H), 4.87 (d, J=11.0 Hz, 1H), 2.99 (dt, J=10.1, 5.1 Hz, 1H), 2.07-1.96 (dqd, J=15.4, 7.5 5.3, 7.5, 15.4 Hz, 1H), 1.24-1.14 (m, 1H), and 1.03 (t, J=7.5 Hz, 3H). 13C-NMR (126 MHz, CDCl3): δ 172.1, 135.8, 133.6, 129.7, 128.8, 128.6, 91.4, 91.4, 81.3, 78.0, 51.8, 19.5, and 12.3; IR (film) 3250 (br), 3032, 2966, 2929, 2877, 1696, 1497, 1455, 1371, 1209, 1104, 1055, 1033 cm-1; HR-ESIMS calculated for C15H17NNaO3 (M+Na)+282.1101; observed 282.1083.

(±)-(4S,5R,1S) 4-(2,2-dimethylethyl)-8-oxo-2-(phenylmethoxy)-2-azabicyclo[3.2.1]oct-6-en-3-one (5c): Prepared in 54% yield (52.7 mg, 0.18 mmol) from the reaction of 2-bromo-2,2-dimethyl-N-(phenylmethoxy)propanamide (103.5 mg, 0.34 mmol) with furan via general procedure B. Rf=0.49 (3:1, hexanes:EtOAc); 1H-NMR (500 MHz, CDCl3): δ 7.43 (m, 2H), 7.41-7.33 (m, 3H), 6.42 (dd, J=6.0, 1.8 Hz, 2H), 6.35 (dd, J=6.0, 1.5 Hz, 1H), 5.20 (d, J=1.3 Hz, 1H), 5.00 (dd, J=4.8, 1.8 Hz, 1H), 4.98 (d, J=11.0 Hz, 1H), 4.88 (d, J=11.0 Hz, 1H), 3.04 (d, J=4.8 Hz, 2H), 1.10 (s, 9H); 13C-NMR (126 MHz, CDCl3): δ 141.6, 136.0, 134.5, 134.0, 129.8, 128.8, 128.6, 91.6, 81.5, 78.0, 60.5, 32.3, and 29.8; IR (film) 3210, 3090, 3064, 3032, 2958, 2871, 1672 (s), 1497, 1480, 1455, 1365 (s), 1231, 1211, 1162, 1054, 1038 cm-1; HR-ESIMS calculated for C17H21NNaO3 (M+Na)+ 312.1455, found 312.1446. HRMS: calculated for C17H21NNaO3 (M+Na)+ 312.1455, found 312.1446

(±)-(4S,5R,1S) 4-chloro-8-oxo-2-(phenyl methoxy)-2-azabicyclo[3.2.1]oct-6-en-3-one (endo-5e) and (±)-(4R,5R,1S) 4-chloro-8-oxo-2-(phenylmethoxy)-2-azabicyclo[3.2.1]oct-6-en-3-one (exo-5e): Prepared in 73% yield (72 mg, 0.31 mmol) from the reaction of 2,2-dichloro-N-(phenylmethoxy)acetamide (100.2 mg, 0.43 mmol) with furan via general procedure B. Rf=0.50 (3:1, hexanes:EtOAc) 1H NMR (400 MHz, CDCl3) δ 7.51-7.30 (m, 3H), 6.54 (dd, J=6.0, 1.1 Hz, 1H), 6.51 (dd, J=6.0, 1.7 Hz, 1H), 5.27 (d, J=1.1 Hz, 1H), 5.09 (dd, J=5.1, 1.6 Hz, 1H), 5.00 (d, J=11.0 Hz, 1H), 4.89 (d, J=11.0 Hz, 1H), and 4.76 (d, J=5.2 Hz, 1H); 13C NMR (101 MHz, CDCl3) δ 165.9, 136.8, 135.3, 133.1, 129.8, 129.2, 128.2, 92.1, 82.1, 78.3, and 56.9; IR (film) 3032, 2950, 2922, 2852, 1712 (s), 1455, 1369, 1213, 1189, 1059, 1023 cm-1. HR-ESIMS calculated for C13H12ClNNaO3 (M+Na)+ 288.0398, found 288.0391. exo-diastereoisomer: Rf=0.3 (3:1, hexanes:EtOAc); 1H NMR (400 MHz, CDCl3): δ 7.48-7.35 (m, 2H), 6.68 (d, J=5.9 Hz, 1H), 6.34 (dd, J=6.0, 1.1 Hz, 1H), 5.28 (s, 1H), 5.02 (d, J=10.9 Hz, 2H), 4.98 (s, 1H), 4.92 (d, J=10.9 Hz, 2H), and 4.09 (s, 1H); 13C NMR (101 MHz, CDCl3) δ 165.5, 138.2, 135.0, 131.4, 129.9, 129.2, 128.8, 91.3, 84.2, 78.4, and 56.1; IR (neat) 3067, 3034, 2946, 2885, 1694, 1046 cm-1; HRMS calculated for C13H12ClNNaO3 (M+Na)+288.0398, observed 288.0399.

(±)-(4S,5R,1S) 4-(4-chlorophenyl)-8-oxo-2-(phenylmethoxy)-2-azabicyclo[3.2.1]oct-6-en-3-one (5f): Prepared in 53% yield (54.4 mg, 0.16 mmol) from the reaction of 2-choro-2-(4-chlorophenyl)-N-(phenylmethoxy)acetamide (95.5 mg, 0.31 mmol) with furan via general procedure B. Rf=0.48 (3:1, hexanes:EtOAc); 1H-NMR (500 MHz, CDCl3): δ 7.50-7.44 (m, 2H), 7.44-7.34 (m, 3H), 7.28 (ABd, J=8.5 Hz, 2H), 7.05 (ABd, J=8.5 Hz, 2H), 6.55 (dd, J=6.0, 1.1 Hz, 1H), 6.19 (dd, J=6.0, 1.7 Hz, 1H), 5.36 (d, J=1.3 Hz, 1H), 5.05 (d, J=11.0 Hz, 1H), 4.96 (d, J=11.0 Hz, 1H), 4.94 (dd, J=5.3, 1.8 Hz, 1H), and 4.38 (d, J=5.3 Hz, 1H); 13C-NMR (126 MHz, CDCl3): δ 169.7, 136.0, 136.0, 135.6, 133.8, 133.8, 132.0, 131.1, 129.83, 129.1, 128.8, 128.7, 91.8, 91.8, 83.1, 83.1, 78.3, and 56.5; IR (film) 3089, 3064, 3031, 2924, 1688, 1492, 1454, 1368, 1275, 1260, 1211, 1091, 1059, 1017 cm-1. HR-ESIMS: calculated for C19H17ClNO3 (M+H)+ 342.0891, observed 342.0886.

(±)-(1R,5S)-4,4-dimethyl-8-oxo-2-(phenylmethoxy)-2-azabicyclo[3.2.1]oct-6-en-3-one (5g): Prepared in 78% yield (85.2 mg, 0.32 mmol) from the reaction of 2-bromo-2-methyl N-(phenylmethoxy)propanamide (115.0 mg, 0.42 mmol) with furan via general procedure B. Rf=0.40 (3:1, hexanes:EtOAc); 1H-NMR (500 MHz, CDCl3): δ 7.46-7.28 (m, 5H), 6.56 (dd, J=5.9, 1 Hz, 1H), 6.43 (dd, J=5.9, 1.9 Hz, 1H), 5.21 (d, J=1.1 Hz, 1H), 4.97 (d, J=10.9 Hz, 1H), 4.87 (d, J=10.9 Hz, 1H), 4.46 (d, J=1.8 Hz, 1H), 1.49 (s, 3H), and 1.05 (s, 3H); 13C-NMR (126 MHz, CDCl3): δ 13C NMR (101 MHz, CDCl3) δ 175.7, 135.7, 135.5, 134.6, 129.8, 128.9, 128.6, 91.5, 87.4, 78.0, 49.3, 27.1, and 19.9; IR (film) 3055 (br), ADD MORE, 1692, 1470, 1385, 1362, 1265, 1217, 1174, 1055, 1008 cm-1; HRMS calculated for C15H17NNaO3 (M+Na)+ 282.1101, observed 282.1098.

(±)-(1'R, 5'S)-spiro[cyclohexane-1,2'-[8]oxo-4'-(phenylmethoxy)-4'-azabicyclo[3.2.1]oct[6]en]-3'-one (5h): Prepared in 65% yield (65.9 mg, 0.22 mmol) from the reaction of 2-bromo-N-(phenylmethoxy)cyclohexane carboxamide (107.2 mg, 0.34 mmol) with furan via general procedure B. Rf=0.62 (3:1, hexanes:EtOAc); 1H-NMR (500 MHz, CDCl3): δ 7.48-7.29 (m, 5H), 6.54 (d, J=5.8 Hz, 1H), 6.43 (dd, J=6.0, 1.7 Hz, 1H), 5.18 (d, J=1.1 Hz, 1H), 4.96 (d, J=10.9 Hz, 1H), 4.93 (d, J=1.4 Hz, 1H), 4.86 (d, J=10.9 Hz, 1H), 2.06 (d, J=12.7 Hz, 2H), 1.89 (td, J=13.5, 6.8 Hz, 3H), 1.75 (s, 2H), 1.62 (dd, J=13.3, 7.5 Hz, 5H), and 1.47-1.19 (m, 6H); 13C-NMR (101 MHz, CDCl3): δ 175.7, 135.8, 135.5, 134.5, 129.8, 128.8, 128.6, 91.2, 82.9, 77.9, 53.3, 33.7, 28.9, 25.5, 21.7, and 21.5; IR (film) 3063, 3031, 2927, 2858, 1690, 1496, 1454, 1367, 1210, 1187, 1076, 1064 cm-1. HR-ESIMS calculated for C18H21NNaO3 (M+Na)+, 322.1414, observed 322.1424.

(±)-(4S,5R,1S) 4-ethyl-2-(phenylmethoxy)-2-azabicyclo[3.2.1]oct-6-en-3-one (endo-5i) and (±)-(4R,5R,1S) 4-ethyl-2-(phenylmethoxy)-2-azabicyclo[3.2.1]oct-6-en-3-one (exo-5i): Prepared in 85% yield (82.3 mg, 0.32 mmol) from the reaction of 2-bromo-N-(phenylmethoxy)butanamide (100.4 mg, 0.37 mmol) with cyclopentadiene via general procedure B. Rf=0.54 (3:1, hexanes:EtOAc); 1H-NMR (500 MHz, CDCl3): δ 7.53-7.28 (m, 5H), 6.30 (dd, J=5.5, 2.0 Hz, 1H), 6.12 (dd, J=5.4, 2.7 Hz, 1H), 4.95 (d, J=10.8 Hz, 1H), 4.88 (d, J=10.8 Hz, 1H), 3.90 (d, J=6.1 Hz, 1H), 2.93 (app q, J=4.2 Hz, 1H), 2.59 (dt, J=10.4, 4.1 Hz, 1H), 2.09 (dt, J=12.1, 7.8 Hz, 1H), 1.99 (dd, J=11.0, 5.3 Hz, 1H), 1.85 (d, J=10.8 Hz, 1H), 1.37-1.16 (m, 2H), and 1.01 (t, J=7.5 Hz, 3H). 13C-NMR (101 MHz, CDCl3): δ 171.6, 137.2, 137.0, 136.0, 129.8, 129.7, 128.7, 128.5, 77.19, 64.5, 51.5, 42.4, 40.8, 21.6, and 12.3; IR (film) 3063, 3031, 2961, 2874, 1668 (s), 1455, 1368. HR-ESIMS: calculated C16H19NaO2 (M+Na)+ 280.1308, found 280.1296. exodiastereoisomer (characterized as a mixture 2.5:1 exo:endo) Rf=0.41 (3:1, hexanes:EtOAc); 1H NMR (500 MHz, CDCl3): d 7.5-7.3 (m, 5H), 6.30 (dd, J=5.5, 2.5 Hz, 1H), 6.17 (dd, J=5.5, 2.9 Hz, 1H), 4.93 (d, J=10.7 Hz, 1H), 4.86 (d, J=10.7 Hz, 1H), 3.86 (br s, 1H), 2.73 (app t, J=4.2 Hz, 1H), 2.20 (dd, J=10.1, 5.3 Hz, 1H), 2.12-2.16 (m, 1H), 2.05-1.98 (m, 1H), 1.92 (d, J=11.3 Hz, 1H), 1.74 (ddd, J=10, 5, 5 Hz, 1H), 1.62-1.59 (m, 1H), 1.31-1.18 (m, 1H), and 1.05 (t, J=7.1 Hz, 3H); 13C NMR 101 MHz, CDCl3) δ 174.5, 138.3, 136.4, 136.0, 129.9, 128.8, 128.5, 77.0, 64.4, 51.5, 42.2, 38.8, 34.3, 30.5, 25.7, 21.6, and 21.3. IR (film) 3063, 3031, 2961, 2874, 1679, 1496, 1455, 1370 cm-1; HRMS calculated C16H19NaO2 (M+Na)+ 280.1308, found 280.1303.

(±)-(4S,5R,1S) 4-chloro-2-(phenylmethoxy)-2-azabicyclo[3.2.1]oct-6-en-3-one and (±)-(4R,5R,1S) 4-chloro-2-(phenylmethoxy)-2-azabicyclo[3.2.1]oct-6-en-3-one (5j): Prepared in 64% yield (73.8 g, 0.28 mmol) from the reaction of 2-bromo-N-(phenylmethoxy)butanamide (100.8 mg, 0.43 mmol) with cyclopentadiene via general procedure B. Rf=0.53 (3:1, hexanes:EtOAc); 1H-NMR (500 MHz, CDCl3): δ 7.46-7.34 (m, 3H), 6.32 (dd, J=5.7, 2.2 Hz, 1H), 6.31-6.28 (m, 1H), 4.98 (d, J=10.9 Hz, 1H), 4.92 (d, J=10.9 Hz, 1H), 4.71 (d, J=4.4 Hz, 1H), 2.06 (dt, J=11.6, 4.8 Hz, 1H), and 1.90 (d, J=11.5 Hz, 1H); 13C-NMR (126 MHz, CDCl3): δ 164.7, 138.0, 136.5, 135.5, 129.9, 129.0, 128.6, 77.4, 65.0, 61.0, 46.8, and 41.7; IR (film) 3066, 3033, 2926, 2853, 1679, 1455, 1372 cm-1; HR-ESIMS calculated for C14H15ClNO2 (M+H)+ 264.0786, found 264.0779.

(±)-(1'R,5'S)spiro[cyclohexane-1,2'-4'-(phenylmethoxy)-4'-azabicyclo[3.2.1]oct[6]en]-3'-one (5k): Prepared in 81% yield (72.9 mg, 0.26 mmol) from the reaction of 2-bromo-N-(phenylmethoxy)butanamide (100.4 mg, 0.32 mmol) with cyclopentadiene via general procedure B. Rf=0.6 (3:1, hexanes:EtOAc); 1H-NMR (400 MHz, CDCl3): 7.42 (d, J=7.5 Hz, 2H), 7.40-7.29 (m, 3H), 6.25 (dd, J=5.6, 2.0 Hz, 1H), 6.16 (dd, J=5.6, 2.9 Hz 1H), 4.92 (d, J=10.4 Hz, 2H), 4.88 (d, J=10.3 Hz, 2H), 3.84 (dd, J=4.2, 3.5 Hz, 1H), 2.98 (dd, J=4.1, 3.1 Hz, 1H), 1.98 (d, J=11.2 Hz, 1H), 1.94 (dt, J=16.6, 12.6 Hz, 1H) 1.88-1.84 (m, 1H), 1.83 (dt, J=10.6, 4.5 Hz, 1H), 1.75 (dq, J=13.4, 3.6 Hz, 1H), 1.70-1.60 (m, 3H), 1.55-1.42 (m, 2H), and 1.42-1.31 (m, 2H); 13C NMR (101 MHz, CDCl3) δ 174.5, 138.6, 136.4, 136.0, 130.0, 128.7, 128.5, 77.0, 64.4, 51.5, 42.3, 38.8, 34.3, 30.5, 25.7, 21.6, and 21.3; IR (film)

3062, 3030, 2925, 2858, 1662 (s), 1454, 1371 cm-1. HRES-IMS calculated for C19H24NNaO2 (M+Na)+ 321.1699, observed 321.1651.

2-methyl-2-(2,2,2-trifluoroethoxy)-N-(phenylmethoxy)-propanamide: Produced as a by-product 56% from the reaction of 2-bromo-2-methyl-N-(phenylmethoxy)propanamide with TEA in furan and trifluoroethanol. Rf=0.26 (3:1, hexanes:EtOAc); 1H NMR (500 MHz, CDCl3) δ 8.88 (s, 1H), 7.56-7.31 (m, 5H), 4.94 (s, 2H), 3.68 (q, J=8.3 Hz, 2H), 1.43 (s, 6H); 13C NMR (125 MHz, CDCl3) 13C NMR (101 MHz, cdcl3) δ 170.8, 134.9, 129.4, 129.0, 128.7, 123.7 (q, J=278 Hz), 80.4, 78.3, 61.6 (q, J=35 Hz), and 23.6; FT-IR 3218 (br), 3036; 2942, 2886, 1663 (st), 1430, 1455, 1485, 1386, 1369, 1307, 1285, 1217, 1181, 1145, 1029, 1010 cm-1; HR-ESIMS calculated for C13H17F3NO3 (M+H)+ 292.1155, observed 292.1160.

2-methyl-N-(phenylmethoxy)-2-propenamide: Elimination product from the reaction attempted cycloaddition of 4g with LiClO4/Et3N in diethyl ether. 1H NMR (400 MHz, CDCl3) δ 8.19 (br s, 1H), 7.49-7.29 (m, 5H), 5.55 (pent, J=1 Hz, 1H), 5.32 (dq, J=1.6, 1.0 Hz, 1H), 4.96 (s, 2H), and 1.92 (dd, J=1.6, 1.2 Hz, 3H); 13C NMR (101 MHz, CDCl3) δ 167.2, 138.0, 135.4, 129.5, 129.0, 128.8, 120.4, 78.3, and 18.6; IR (film) 3199 (br), 3064, 3032, 2954, 2878, 1658, 1620, 1496, 1453, 1372, 1322, 1209, 1039 cm-1; HR-ESIMS calculated for C11H13NNaO2 (M+Na)+ 215.0871, found 215.0869.

Mono-alkyl substituted bromohydroxamates (entries a-e, Table 1) provided the highest yields of the cycloadduct under the recited conditions. With the exception of entry e ($R^1$=Cl), all mono-substituted halohydroxamates (entries a-d and f) selectively provided the endo-diastereoisomer (≥19:1 by crude 1H NMR analysis). In the case of entry e, a diasteriomeric ratio of the cycloaddition was observed to vary over the course of the reaction; at early conversion (ca. 40% conversion), a diasteriomeric ratio of ≥19:1 d.r. was observed, but at 100% conversion, the diasteriomeric ration was ca. 2:1, endo:exo. Treatment of the pure endo-adduct to the reaction conditions provided an epimeric mixture (ca. 1:1, endo:exo) after 24 h, suggesting that the α-stereogenic center of the endo-product is epimerizing during the reaction. The monosubstituted hydroxamates were slower to react and did not solvolyze in trifluoroethanol. Changing the halogen from bromide to chloride ultimately provided a comparable yield of the product after 48-72 h (entries e and f). Unsubstituted mono-bromohydroxamate (X=Br, $R^1$=R2=H) was found to be un-reactive under these conditions. This result is consistent insofar as the un-substituted oxyallylcation does not have the added stabilization afforded by groups such as alkyl substituents, and the dehydrohalogenation of α-bromoacetamide also did not result in a [4+3] cycloaddition with furan. In constrast, fully-substituted and aryl-substituted α-halohydroxamates rapidly reacted under the conditions to provide the corresponding cycloadduct in moderate yield. The best results for these fully-substituted and aryl-substituted α-halohydroxamates were observed in HFIP (entries f-h). The increase in rate of conversion of these substrates is presumably due to the stabilizing effect that substitution ($R^1$=$R^2$=alkyl, entries g and h) or delocalization (entry f) has on the aza-oxyallylcationic intermediate.

The aza-[4+3] cycloaddition of α-halohydroxamates with cyclopentadiene afforded the cycloadducts in comparable yield to the corresponding furan reactions (entries i-k, Table 1). The ethyl-substituted α-halohydroxamate provided the cyclopentadiene aza-[4+3] cycloadduct in identical yield but with less diastereoselectivity than its reaction with furan (entry i). The aza-[4+3] cycloaddition reaction of the α,α-dichlorohydroxamate with cyclopentadiene provided a mixture of diastereoisomeric cycloadducts at full conversion (8:1, entry j) of starting material. Again, the reaction time of the bromo-cyclohexane hydroxamate was considerably shorter than what was observed for the reaction of the ethyl-substituted hydroxamate (cf entry i and k, Table 1).

With reference now to Table 2 below, the effect of solvent and the nature/amount of the activator was further explored with respect to compound 4g from Table 1.

TABLE 2

Effect of solvent and activator on the yield of the aza-[4 + 3] cycloaddition reaction of 2-bromobutyramide 4g with furan.

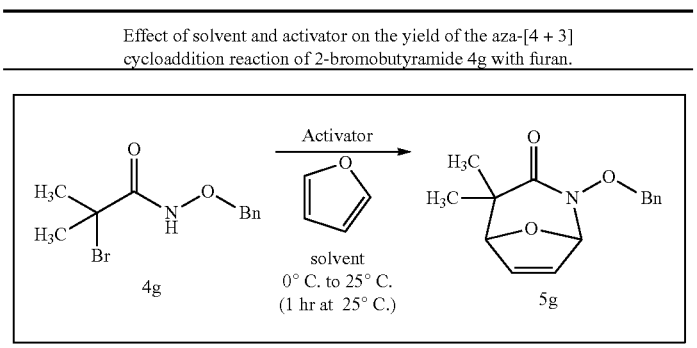

| Entry[a] | Solvent | Activator | Yield[b] % |
|---|---|---|---|
| 1 | TFE | Et3N | 38%[c] |
| 2 | HFIP | Et3N | 78% |
| 3 | HFIP | Cs2CO3 | 58% |
| 4 | HFIP | K2CO3 | 67% |
| 5 | HFIP | Na2CO3 | 74% |
| 6 | TFE | imidazole | decomp. |
| 7 | TFE | pyridine | no reaction |
| 8 | Et2O | Et3N, LiClO4 | See text |

[a]All reactions were conducted in solvent:furan (1:1 v/v, 0.25 M) at 0° C. with activator (2.0 equiv)
[b]Isolated yield of the cycloadduct 5g.
[c]Provided a 56% yield of CF3CH2OH solvolysis product.

The treatment of the α-bromohydroxamate 4g to Fölisch-type [4+3] cycloaddition conditions (TFE/TEA) in the presence of furan resulted in a rapid consumption of starting material, providing a 38% yield of the desired cycloadduct 5. A trifluoroethylether 6 (56%) was formed as the major product of this reaction, and presumed to be the result of solvolysis of the intermediate or the N-benzyloxyaziridinone. The choice of activator and solvent influences the yield of the cycloadduct. Changing to hexafluoroisopropanol (HFIP) as the solvent slowed the formation of the solvolysis product and significantly improved the yield of the cycicoadduct (cf entry 1 with 2-5, Table 2); the iso-propyl ether 6 was not detected by crude $^1$H NMR analysis. Various amine bases, with the exception of pyridine and imidazole, were found to successfully induce the desired cycloaddition reaction. Carbonate bases worked well, all providing desired product in comparable yield (entries 3-5, Table 2) to the reaction using triethylamine. The reaction could be effected in ether by using triethylamine with lithium perchlorate as a Lewis-acid additive, but these conditions also provided a methacrylamide 7 as the major product from the elimination of the cationic intermediate or a transient α-lactam.

As demonstrated herein, α-halohydroxamates such as N-benzyloxy α-bromoamides react under basic conditions with cyclic dienes to provide bicyclic lactams in good yield. Without being bound by any particular theory, one plausible mechanism is that an aza-oxyallylcationic intermediate is formed upon dehydrohalogenation of the α-halohydroxamates and that this aza-oxyallylcationic intermediate undergoes an aza-[4+3] cycloaddition reaction with dienes. The heteroatom-substitution on the nitrogen group is presumed to stabilize the aza-oxyallylcationic intermediate.

The aza-[4+3] cycloadducts are suitable intermediates for the synthesis of biologically-active molecules. For example, the aza-[4+3] cycloadducts are suitable intermediates for the synthesis of nitrogen-containing compounds, such as balanol which possesses potent protein kinase C inhibition activity (see Boros, C. et al., *J. Antibiot.* 1994, 47, 1010), and banisternosides A and B which possess MAO inhibitory and antioxidative activities relevant to neurodegenerative disorders and Parkinson's disease (see Samoylenko, V. et al. *J. Ethnopharm.* 2010, 127, 357), as well as analogues and/or derivatives thereof. Other exemplary targets include anti-viral carbocyclic nucleosides such as carbovir, aristeromycin and BMS-200475, or glycosidase inhibitors such as deoxynojirimycin, miglitol, and poly-hydroxylated azepanes, obtainable from the aza-[4+3] cycloadducts of α-halohydroxamates with cyclopentadiene and furan, respectively.

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and/or method and examples shown and described. The various features of exemplary embodiments described herein may be used in any combination. Accordingly, departures may be made from such details without departing from the scope of the general inventive concept.

What is claimed is:
1. A compound represented by structural Formula (I):

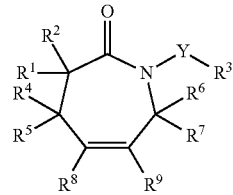

Formula (I)

wherein
$R^1$ and $R^2$ are the same or different and are independently selected from hydrogen, halide, a substituted or un-substituted alkyl, aryl, alkaryl, alkenyl, alkynyl, amino, carboxamido, alkoxy, alkylthio, mercapto, or RC(O)O—, RC(O)—, or $(R)_3Si$—, wherein each R independently is selected from alkyl, alkenyl, alkynyl, or aryl; or $R^1$ and $R^2$ in combination form a $C_3$-$C_6$cycloalkyl;

$R^3$ is a substituted or unsubstituted alkyl, aryl, alkaryl, alkenyl, alkynyl, sulfinyl, sulfonyl, or RC (O)—, or $(R)_3Si$—, Wherein each R independently is selected from alkyl, alkenyl, alkynyl, or aryl;

$R^4$ and $R^6$ are the same or different and are independently selected from hydrogen, halide, a substituted or un-substituted alkyl, carboxyl acyl, aryl, alkaryl, alkenyl, alkynyl, amino, carboxamido, alkoxy, acyloxy, alkythio, mercapto, or hardocarbyl silyl; $R^5$ and $R^7$ together represent —$CH_2$—, —O—, NH —or S—;

$R^8$ and $R^9$ are the same or different and are independently selected from hydrogen, halide, a substituted or un-substituted alkyl, aryl, alkaryl, alkenyl, alkynyl, amino, carboxamido, alkoxy, alkylthio, mercapto or or RC (O) O—, RC (O)—, or (R) Si—, wherein each R independently is selected from alkyl, alkenyl, or aryl; and Y is O, S, SO, or $NR^{10}$, wherein $R^{10}$ is a hydrogen, a substituted or unsubstituted aryl, alkaryl, alkenyl, alkynyl, sulfinyl, sulfonyl, unsubstituted alkyl, or $(R)_3Si$—, wherein each R independently is selected from alkyl, alkenyl, or alkynyl, or aryl.

2. The heterocyclic compound of claim 1, wherein $R^1$ and $R^2$ in combination form a cyclohexyl.

3. The heterocyclic compound of claim 1, wherein $R^5$ and $R^7$ is —O—or —$CH_2$—.

4. The heterocyclic compound of claim 1, wherein $R^1$ and $R^2$ are independently selected from hydrogen, halide, a substituted or un-substituted alkyl, aryl, alkaryl, alkenyl, alkynyl, amino, alkoxy, or RC(O) O—, wherein each R independently is selected from alkyl, alkenyl, alkynyl, or aryl, or $R^1$ and $R^2$ in combination form a cyclohexyl ring;
wherein $R^3$ is a substituted or unsubstituted alkyl, aryl, alkaryl, alkenyl, alkynyl, sulfinyl, or sulfonyl;
wherein $R^4$ and $R^6$ are independently selected from hydrogen, halide, a substituted or un-substituted alkyl, aryl, alkaryl, alkenyl, alkynyl, amino, alkoxy, or RC(O)-O—, wherein each R independently is selected from alkyl, alkenyl, alkynyl, or aryl;
wherein $R^8$ and $R^9$ are independently selected from hydrogen, halide, a substituted or un-substituted alkyl, aryl, alkaryl, alkenyl, alkynyl, amino, alkoxy, or RC(O) O—, wherein each R independently is selected from alkyl, alkenyl, alkynyl or aryl; and wherein $R^{10}$ is a hydrogen, a substituted or unsubstituted aryl, alkaryl, alkenyl, alkynyl, sulfinyl, or sulfonyl, or an unsubstituted alkyl.

* * * * *